United States Patent [19]

Garrett et al.

[11] 4,052,617
[45] Oct. 4, 1977

[54] LETTUCE MATURITY GAGE

[75] Inventors: Roger E. Garrett, Davis; Paul Christensen, El Macero, both of Calif.

[73] Assignee: The Regents of the University of California, Berkeley, Calif.

[21] Appl. No.: 727,683

[22] Filed: Sept. 29, 1976

[51] Int. Cl.² ........................................... G01N 23/00
[52] U.S. Cl. ............................... 250/360; 209/111.5; 250/493; 250/498
[58] Field of Search ............... 250/360, 498, 358, 493; 209/111.5

[56] References Cited
U.S. PATENT DOCUMENTS 3,594,579  7/1971  Garrett .............................. 209/111.5

Primary Examiner—Harold A. Dixon

Attorney, Agent, or Firm—Lothrop & West

[57] ABSTRACT

For use with lettuce heads growing in double rows between furrows, there is provided a wheeled cart having a body adapted to be drawn along a furrow and carrying a radiant energy detector and an indicator, printer or readout for the detector, as well as a power supply and auxiliary equipment for the indicator and detector. One or a pair of outrigger bodies are articulated to and movable toward and away from the cart body. Each outrigger body runs between the lettuce heads in one of the double rows on opposite sides of the furrow. A source of radiant energy is located in one or both outrigger bodies and beams through the lettuce heads to the detector. Except when away from the cart body in operating position, the energy source is or the sources are shielded to block release of radiant energy. The source and detector locations may be interchanged.

9 Claims, 6 Drawing Figures

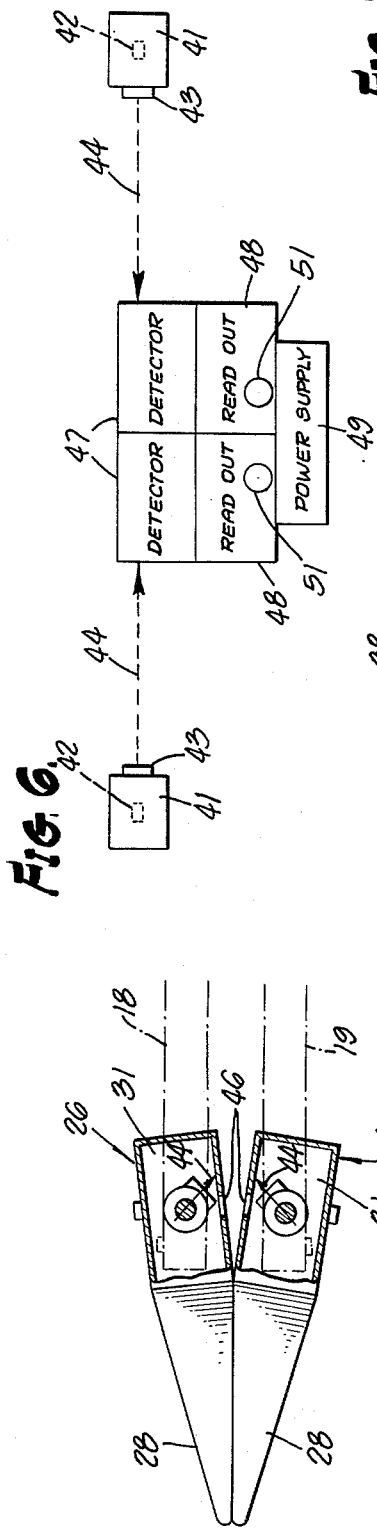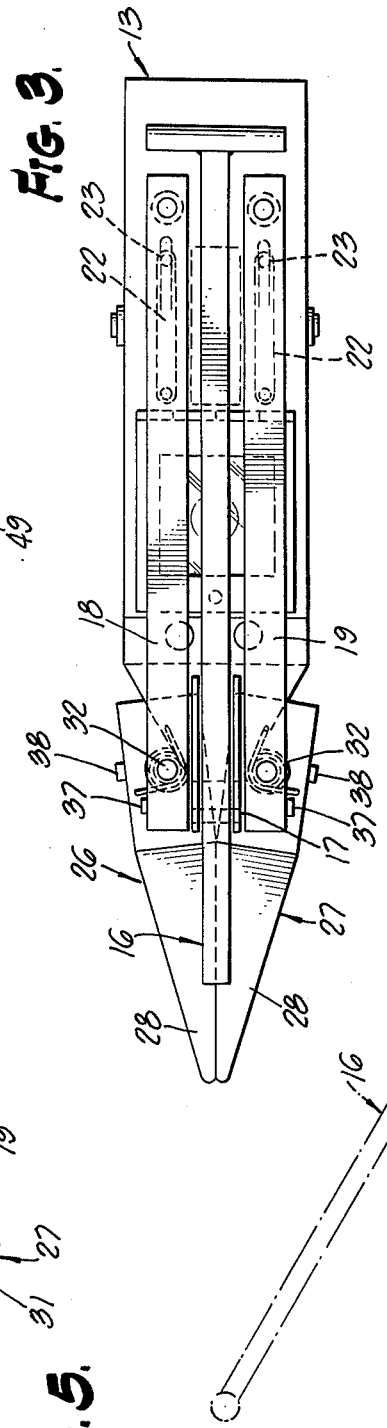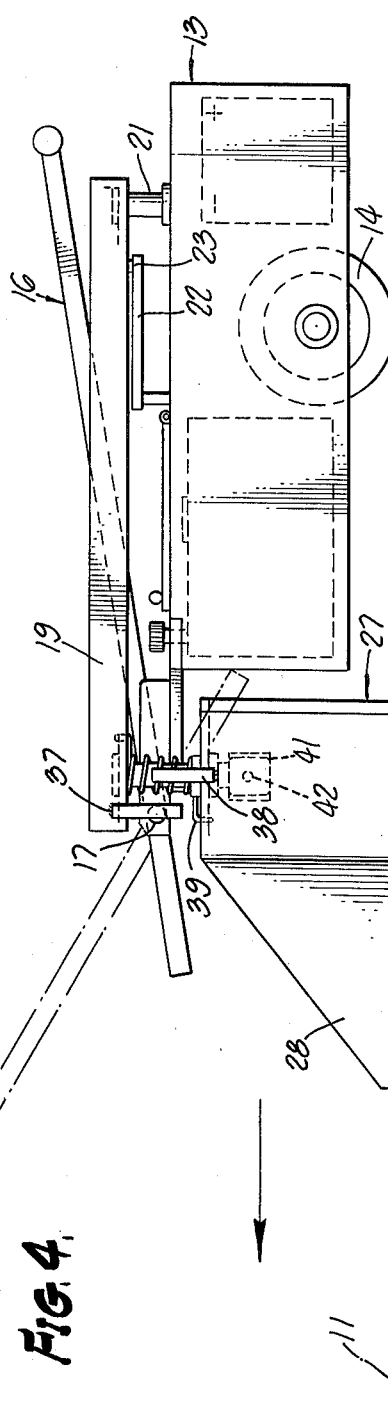

LETTUCE MATURITY GAGE

BRIEF SUMMARY OF THE INVENTION

A source of radiant energy and a detector therefor are movable with respect to each other, and except for one position relative to the detector the source is completely shielded. The source and receiver are made portable on a cart which is drawn between double rows of lettuce growing in a field. The radiation from the source is attenuated by the lettuce heads in accordance with their maturity or density, so gives corresponding variable signals to the detector. A readout or other indicator responding to the detector yields a showing as to lettuce maturity. The unit is light and portable and is self-contained. The radiation material is carefully and safely shielded except for a collimated beam released only during maturity testing.

BRIEF DESCRIPTION OF THE SEVERAL VIEWS OF THE DRAWING

FIG. 3 is a plan of the gage as it appears when in compactly folded condition.

FIG. 4 is a side elevation of the structure shown in FIG. 3.

FIG. 5 is a detail with portions broken away to show the interior arrangement of the forward part of the mechanism in the position illustrated in FIG. 3.

FIG. 6 is a diagram showing the relationship of a radiation detector and indicator and a radiation source.

DETAILED DESCRIPTION

Figure 1:
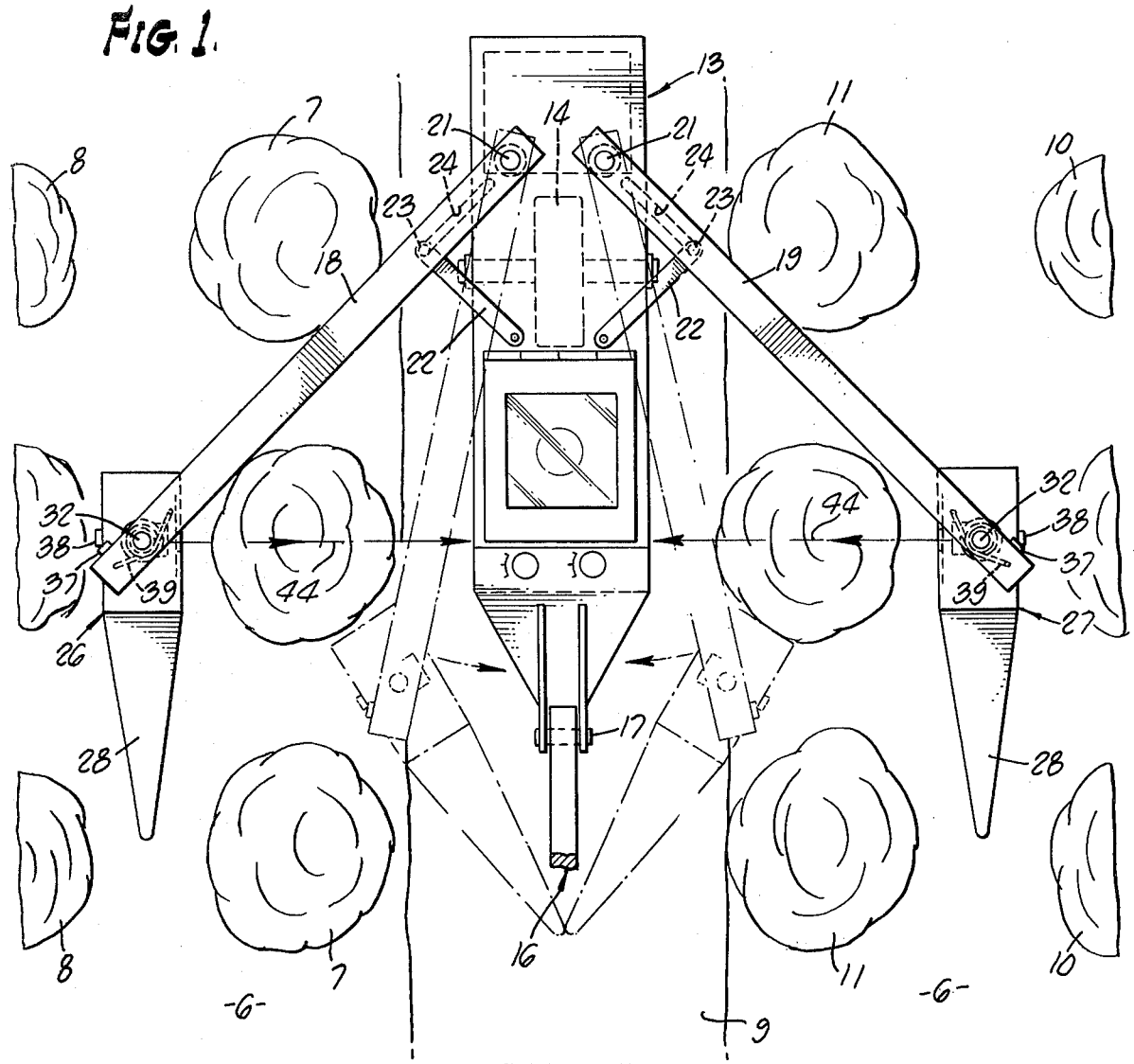
FIG. 1 is a plan of a lettuce maturity gage pursuant to the invention showing the device in a field with lettuce growing in double rows alongside a furrow and with the device extended for use, certain broken lines showing an intermediate position.

It is important to know the state of maturity of lettuce heads growing in rows between furrows in the growing field in order that the lettuce harvest can be conducted at an optimum time and so that the lettuce heads appropriate for harvesting can be separated from those heads which are not ready for harvesting. Various means have been devised for doing this, but most of them are cumbersome or inaccurate or difficult to utilize. An appropriate detection method involves the use of a source of radiant energy. Some work has been accomplished utilizing X-rays, but there are some objections to that. Other work has been accomplished by using radioactive material as set forth in the Garrett et al. U.S. Pat. No. 3,594,579. While there is good coordination between the amount of radiation intercepted by a mature lettuce head and that intercepted by an immature head, there are difficulties involved in utilizing a radioactive source, partly because of actual or supposed hazards.

It is therefore an object of the invention to provide a lettuce maturity gage which is very readily used and can be taken from field to field and from one part of a field to another and easily operated in connection with the lettuce rows to provide a test in the field on the growing lettuce heads.

Another object of the invention is to provide such a maturity gage in which a radioactive source is utilized but in which the source is extremely well guarded and protected so that there is no hazard from random radiation.

A further object of the invention is to provide a maturity gage of the sort indicated in which there is a self-contained unit involving virtually all of the indicating or readout structures so that there is no exposed electrical wiring or the like.

A further object of the invention is to provide a maturity tester in which the blocking or radiation shielding mechanism functions automatically.

Other objects, together with the foregoing, are attained in the form of the invention shown in the accompanying drawings and described in the following description.

While the maturity gage can be utilized with crops other than lettuce, especially those of a similar character and arranged in rows and developing heads, nevertheless the device is described particularly as it is shaped for use in connection with lettuce. Customarily, lettuce is cultivated in a field by being planted in the ground 6 in parallel, double rows 7 and 8 of lettuce heads separated by a central furrow 9 from a similar double row of lettuce heads 10 and 11. The cultivation varies from area to area as to arrangement of rows and furrows and as to transverse dimensions. The usual spacing is approximately as shown in the figures, the double rows being quite close together so the outer, wrapper leaves of large heads may even touch.

For use in this environment, there is provided a cart body 13 which in general is an elongated, rectangular enclosure of relatively narrow width so as easily to fit in the furrow 9 between the adjacent rows 7 and 11 of lettuce. The cart body is primarily supported on a single wheel 14 adapted to run on the bottom of the furrow 9 with the cart body slightly above the subjacent ground. The body is impelled in one direction by hand power by means of a handle 16 mounted on the body by a hinge 17 so that the handle can be folded over for compactness in transport, as shown in FIGS. 3 and 4.

To assist in stabilizing the cart body and for other reasons, there is mounted on the body a pair of outrigger arms 18 and 19 disposed in a symmetrical fashion. A description of one arm applies to the other as well. Each arm is joined to the body 13 by means of a pivot pin 21 so that the arm can move about a vertical axis between a stowed or close position as shown in FIG. 3 and an extended or far position as shown in FIG. 1. The extent of movement of each of the outrigger arms is limited by a pivoted link 22 joined to the body at one end and at the other end having a pin 23 sliding in a slot 24 in the arm itself. In this way the arms can be moved into a close position adjacent the body and then can be spread apart to a far position away from the body but nevertheless are limited in spread so that a pull on the handle 16 is effective to draw the arms along in set maximum positions with the body.

At their outer ends the respective arms are provided with outrigger bodies 26 and 27. These are substantially identical so that the description of one applies to the other. Each of the bodies 26 and 27 is a hollow, generally rectangular enclosure having a tapered forward portion 28 so that the outrigger can advance easily between the flexibly projecting outer leaves of the heads on opposite sides of the outrigger. The body 27, for example, has a bottom plate 31 adapted to rest on the top of the underlying ground or bed so that the bottom plate acts as a sort of stabilizing skid.

The body 27 is related to the adjacent outrigger arm 19 by means of a connection around a vertical axis 32 parallel to the axis of the pins 21. While the body 27 can rotate around the axes 21 and 32 with respect to the outrigger arm and the body 13, the pivot connections are sufficiently rigid in a vertical direction so that the outriggers serve as spaced, lateral supports for the mechanism. This avoids lateral tipping, yet the device can follow irregularities in the ground without difficulty since the support is substantially at three points. The machine always orients properly and can be easily advanced even though the ground is somewhat uneven.

The construction within at least one of the outriggers is special in that the related one of the outrigger arms, such as 19, has the pivot connection with the outrigger body 27 formed by a fixed tube 33. This extends into the interior of the outrigger body and is journalled therewith. The pivot connection is supplemented by a pair of bearing washers 34 and 36 so that the vertical alignment is preserved. The parts are thus made relatively rotatable about the axis 32. The limit of relative motion is fixed by stops 37 and 38 in the outermost direction so that the longitudinal dimension or long axis of each of the outrigger bodies is parallel to the longitudinal dimension or long axis of the cart body 13. The parts are urged into one particular extreme position with stops in abutment by a spring 39 disposed around the tube 33 and engaging both the outrigger arms and the outrigger body.

Particularly pursuant to the invention, there is located within at least one of the outrigger bodies, preferably at the end of the tube 33, a holder 41 containing a radioactive source 42. This source material is preferably Americium 241. The source is particularly packed in a capsule fixed within the holder 41 and is arranged at a suitable location and height so that the capsule is entirely enclosed and shielded except for a window 43 in the side of the holder, from which radiation can emanate in the form of a beam 44. The beam can get beyond the outrigger body 27, however, only when the source window 43 is lined up with an opening 46 in the body 27. This occurs only when the outrigger body in the outermost position thereof is substantially parallel to the cart body. The beam 44 is at an appropriate height to travel through the lettuce head 7, for example, at approximately the maximum diameter of the lettuce head.

Sometimes, the source is located outside the tube 33 which itself may contain a controlling aperture. The fundamental operation is as described in that the radiation beam is always blocked or completely confined except when the beam can pass directly to and through an adjacent lettuce head.

The radiation energy is attenuated by the lettuce head in accordance with the density or maturity thereof. The remaining portion of the beam, after attenuation, is received in the cart body by an appropriate receiver or detector 47. A similar or duplicate arrangement may, if desired, be provided on the other outboard arm 18 so that a similar source sends a beam traversing the lettuce head 11 and also is effective upon a duplicate of the detector or receiver 47. Each receiver is of a known kind connected by appropriate circuitry to a related indicator, printer or readout 48 graduated in maturity units or in any other convenient indicative numbers. A power source 49 is included in the cart body. There can likewise be included in one or both indicators a relatively small calculator or calculators into which factors can be preinserted so that the readout, printout or readouts can be in any desired terms. With this arrangement, there can also be provided adjustments 51 to calibrate the mechanism or to arrange the response to any desired threshold of maturity prior to indication or readout. The arrangement is such that there is no wiring which extends outside of the cart body.

In the customary utilization of the device, it is initially received at the field in folded condition, the two outboard bodies 26 and 27 being then necessarily in their approached or inner position, as shown in FIGS. 3 and 5. In this position they abut and automatically turn each other about their pivot axes 32. There is no alignment between the window 43 and the opening 46. The source 42 is blocked from emanating to the exterior. The device is entirely safe. Sometimes it is desired to have the relative rotation take place well within the holder 41 by a sleeve moving with the body 27, but the present showing is, at least diagrammatically, to the same end.

Figure 2:
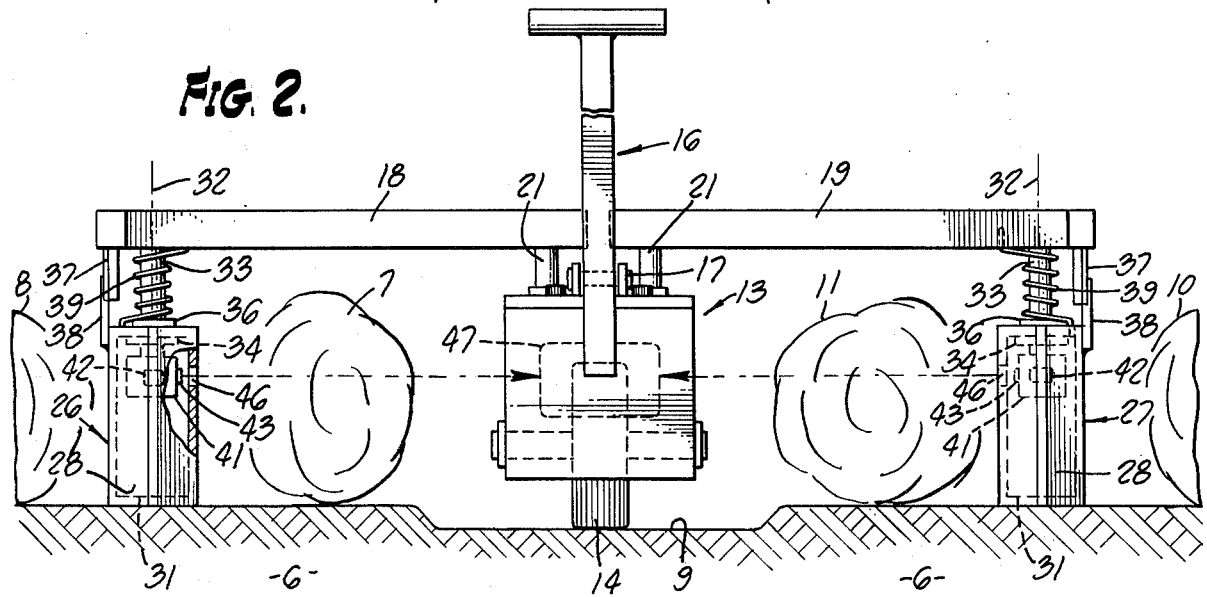
FIG. 2 is a front elevation of the structure shown in FIG. 1, certain portions being broken away to disclose some interior construction, and other parts being broken away to reduce the figure size.

In the folded condition, since there is no emanation and since the package is quite compact, the cart can be easily put down in a furrow with the wheel 14 resting on the ground. The outriggers are or have previously been moved out to their open position as shown in FIG. 1 and are braced in position by the links 22. During this outward motion, the opening 46 is rotated with respect to the window 43 about the axis 32 so that radiation from the source 42 can travel outwardly toward the receiver 47. This is true on both sides of the device if the device is duplex. The outriggers then rest at the top of the adjacent lettuce beds substantially in the attitude shown in FIG. 2, and the handle 16 is extended.

When the adjustments 51 have been set and the main switch has been closed, the device is entirely operative. The operator then walks backward in the furrow 9, drawing the machine behind him. The device runs and slides over the surface of the ground without difficulty, the inclined points 28 of the outrigger bodies parting the lettuce wrapper leaves so that forward progress is not impeded. As the machine passes each lettuce head or pair of lettuce heads, the radiation from the adjacent source travels through it or them, is attenuated and the net radiation is effective upon the receiver or receivers to afford an appropriate maturity readout or a comparable number, depending upon the program introduced.

When readings have been taken in a desired area, the machine is taken from the furrow and the outrigger arms are folded in after the links 22 have been tripped. When that occurs, the outrigger bodies come into contact and rotate each other with respect to the outrigger arms to misalign the windows and apertures. Radiation is then confined within the source itself and does not get to the exterior. The device can then be picked up and carried easily by one person to another area for exploration, and the operation can be repeated.

Under some circumstances, the location of the source and receiver can be interchanged in that a source may be located in the cart body and its receiver may be located in an outrigger body. The shielding is arranged, as before, so that the relative motion between the cart body and an outrigger body allows radiation from the source only when the device is deployed for use and not otherwise; that is, the source is shielded except when the cart body and outrigger body are a maximum distance apart.

We claim:

1. A lettuce maturity gage comprising a cart body, means for supporting said cart body on the ground alongside a row of growing lettuce, means for advancing said cart body along said row, an outrigger body, means for articulating said outrigger body on said cart body for movement between an inner position near said cart body and an outer position away therefrom, a source of radiant energy in one of said bodies, a radiant energy receiver on the other of said bodies in position to receive energy radiated from said source, means for blocking radiation of energy from said source, and means for controlling the operation of said blocking means in accordance with the operation of said articulating means.

2. A device as in claim 1 including means for indicating the response of said receiver to receipt of radiant energy.

3. A device as in claim 1 in which said outrigger body and said articulating means are interconnected by a pivot, and said blocking means rotates in accordance with rotation of said pivot.

4. A device as in claim 1 in which said articulating means includes parts rotatable about a pivot axis, said source bears a predetermined relationship to said axis, and said blocking means and said source rotate relative to each other about said axis.

5. A device as in claim 1 in which said blocking means is interposed between said source and said receiver except when said outrigger body is substantially in said outer position.

6. A device as in claim 1 in which said articulating means includes an outrigger arm at one end pivoted on said cart body and at the other end pivoted on said outrigger body, means effective in said inner position for pivoting said outrigger body in one direction on said outrigger arm, and a spring effective out of said inner position or pivoting said outrigger body in the opposite direction on said outrigger arm.

7. A lettuce maturity gage comprising a cart body, a wheel mounted on said cart body for supporting said cart body on the ground, a pair of outrigger arms, means for pivoting said outrigger arms on said body to swing between inner positions close to said body and outer positions away from said body, a pair of outrigger bodies, means for pivoting said outrigger bodies on respective ones of said outrigger arms, a source of radiant energy on each of said outrigger bodies and adapted to send beams of radiant energy toward said cart body from said outer positions of said outrigger bodies, a pair of radiant energy receivers in said cart body in the paths of said beams when said outrigger bodies are in said outer positions, and means on said cart body and connected to said receivers for responding to radiant energy reception by said receivers.

8. A device as in claim 7 in which said outrigger bodies are positioned to rest on the ground at either side of said cart body when said outrigger arms are in said outer positions.

9. A lettuce maturity gage comprising a cart body, means for supporting said cart body directly on the ground, an outrigger arm, means for pivoting said outrigger arm on said cart body to swing between an inner position close to said cart body and an outer position away from said cart body, an outrigger body, means for pivoting said outrigger body on said outrigger arm, a source of radiant energy in one of said bodies adapted to send a beam of radiant energy in a predetermined path, means in said path for blocking said beam adjacent said source, a radiant energy receiver in the other of said bodies, means for removing said blocking means from the path of said beam when and only when said outrigger body is in said outer position, and means on said cart body and connected to said receiver for responding to radiant energy reception by said receiver.

* * * * *